(12) United States Patent
Ikeda et al.

(10) Patent No.: US 7,247,466 B2
(45) Date of Patent: Jul. 24, 2007

(54) AMINO ACID RACEMASE HAVING LOW SUBSTRATE SPECIFICITY AND PROCESS FOR PRODUCING RACEMIC AMINO ACID

(75) Inventors: Hajime Ikeda, Hofu (JP); Yoshiyuki Yonetani, Machida (JP); Shin-ichi Hashimoto, Hofu (JP); Makoto Yagasaki, Machida (JP); Kenji Soda, Uji (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/506,152

(22) PCT Filed: Feb. 28, 2003

(86) PCT No.: PCT/JP03/02333

§ 371 (c)(1),
(2), (4) Date: Sep. 1, 2004

(87) PCT Pub. No.: WO03/074690

PCT Pub. Date: Sep. 12, 2003

(65) Prior Publication Data

US 2005/0095670 A1    May 5, 2005

(30) Foreign Application Priority Data

Mar. 1, 2002   (JP) .............................. 2002-056293

(51) Int. Cl.
*C07H 21/04* (2006.01)
*C12N 9/90* (2006.01)
*C12N 15/74* (2006.01)
*C12N 1/21* (2006.01)
*C12P 21/06* (2006.01)

(52) U.S. Cl. ............ 435/233; 435/252.33; 435/252.34; 435/320.1; 435/69.1; 435/252.3; 435/419; 435/325; 435/348; 436/23.2

(58) Field of Classification Search .................... None
See application file for complete search history.

(56) References Cited

FOREIGN PATENT DOCUMENTS

JP           57-83288        5/1982

OTHER PUBLICATIONS

J. Bactrol. 1993, 4213-4217 ( It is in IDS ( 1449).*
Nelson et al. (Environ Microbiol 2002, vol. 4, pp. 799-808).*
Nagata et al. (Agric boil. Chem. 1985, vol. 49, pp. 1137-1141).*
Roise, et al., "Inactivation of the *Pseudomonas striata* Broad Specificity Amino Acid Racemase by D and L Isomers of β-Substituted Alanines: Kinetics, Stoichiometry, Active Site Peptide, and Mechanistic Studies", American Chemical Society, Biochemistry 1984, vol. 23, o. 22, pp. 5195-5201.

T. Nakamura, et al., "Racemization of Cysteine and Selenocysteine by Low-substrate-specific Amino Acid Racemase", Sulfur Amino Acids, 1984, vol. 7, No. 2, pp. 443-447, Aug. 25, 1984, with English Abstract.

Nelson, et al., "Complete genome sequence and comparative analysis of the metabolically versatile *Pseudomonas putida* KT2440", Environmental Microbiology (2002), vol. 4, No. 12, pp. 799-808, Oct. 10, 2002.

T. Kazuoka, et al., "Low-substrate-specific Amino Acid Racemase Derived from *Pseudomonas putida*", Seikagaku (Biochemistry), Aug. 2002, vol. 74, No. 8, p. 987, 4P-116, with English Abstract.

M. Nakamura, et al., "Low-substrate-specific Amino Acid Racemase of *Pseudomonas putida* IFO12996 : Its Enzymatic properties and Structure", Vitamin, Mar. 25, 2002, vol. 76, No. 3, p. 176, 083, with English Abstract.

M. Nakamura, et al., "Low-substrate-specific Amino Acid Racemase of *Pseudomonas putida* IFO12996 : Its Purification and Enzymatic Characteristics", Japan Society for Bioscience, Biotechnology and Agrochemistry, Mar. 5, 2002, p. 36, with English Abstract.

Soda, et al., Amino Acid Racemase (*Pseudomonas striata*), Amino Acid Racemase, vol. 222, pp. 629-636, Agr. Biol. Chem. (Tokyo) vol. 31, No. 1097, 1971.

Lim, et al., "A New Amino Acid Racemase with Threonine α-Epimerase Activity from *Pseudomonas putida*: Purification and Characterization", Institute for Chemical Research, vol. 175, No. 13, pp. 4213-4217, Journal of Bacteriology, Jul. 1993.

Inagaki, et al., "Purification and Characterization of Amino Acid Racemase with Very Broad Substrate Specificity", Agric. Biol. Chem., vol. 51, No. 173, pp. 173-180, 1987.

U. Strych, et al., "Characterization of the alanine racemases from two Mycobacteria", FEMS Microbiology Letters, vol. 196, No. 2, pp. 93-98, 2001 (XP-002364660); sequence listing, 2 pp. (XP002364619); and *European Bioinformatics institute*, Alignment Display, (sequence listing), 3 pp..

U. Strych, et al., "Characterizatoin of the Alanine Racemases from *Pseudomonas aeruginosa* PAO1", Current Microbiology, vol. 41, No. 4, pp. 290-294, 2000 (XP-002364661); sequence listing, 2 pp. (XP-002364620); and *European Bioinformatics Institute*, Alignment Display, (sequence listing), 2 pp.

* cited by examiner

*Primary Examiner*—Rebecca A. Prouty
*Assistant Examiner*—Md. Younus Meah
(74) *Attorney, Agent, or Firm*—Antonelli, Terry, Stout & Kraus, LLP.

(57) ABSTRACT

The present invention provides a protein having low-substrate-specific amino acid racemase activity; DNA encoding the protein; a recombinant DNA comprising the DNA; a transformant carrying the recombinant DNA; a process for producing the protein by using the transformant; and a process for producing a racemic amino acid which comprises allowing a culture of the transformant or a treated matter thereof as an enzyme source and an amino acid to be present in an aqueous medium to racemize the amino acid in the aqueous medium, and recovering the racemic amino acid from the aqueous medium.

18 Claims, 2 Drawing Sheets

AMINO ACID RACEMASE HAVING LOW SUBSTRATE SPECIFICITY AND PROCESS FOR PRODUCING RACEMIC AMINO ACID

TECHNICAL FIELD

The present invention relates to a protein having low-substrate-specific amino acid racemase activity, DNA encoding the protein, a recombinant DNA comprising the DNA, a transformant carrying the recombinant DNA, a process for producing a protein having low-substrate-specific amino acid racemase activity by using a transformant which expresses the protein having low-substrate-specific amino acid racemase activity, and a process for producing a racemic amino acid by using the transformant.

BACKGROUND ART

Low-substrate-specific amino acid racemase, which is classified as EC 5.1.1.10 and whose substrate specificity is very low, is an enzyme useful for the industrial production of racemates of various amino acids. The microorganisms so far reported to produce this enzyme are strains belonging to the genera *Pseudomonas* [Methods in Enzymology, 17B, 629–636 (1971); Journal of Bacteriology, 175, 4213–4217 (1993)] and *Aeromonas* [Agricultural Biological Chemistry, 51, 173–180 (1987)]. However, their activity is often weak, and it is difficult to fully compensate this defect by improvement of culturing method or acquisition of a mutant strain.

With regard to the proteins having low-substrate-specific amino acid racemase activity, the protein produced by *Pseudomonas putida* IFO12996 has been purified and the amino acid sequence of its active site has been reported [Biochemistry, 23, 5195–5201 (1984)]. However, there has been no report on the DNA sequence encoding the enzyme or on a successful high-level expression of a protein having the enzyme activity using a microorganism such as *Escherichia coli*.

DISCLOSURE OF THE INVENTION

An object of the present invention is to provide a protein having low-substrate-specific amino acid racemase activity, DNA encoding the protein, a recombinant DNA comprising the DNA, a transformant carrying the recombinant DNA, a process for producing a protein having low-substrate-specific amino acid racemase activity by using a transformant which expresses the protein having low-substrate-specific amino acid racemase activity, and a process for producing a racemic amino acid by using the transformant.

The present inventors made intensive studies to solve the above-described problem and have discovered a gene product which shows homology to an internal sequence of a known low-substrate-specific amino acid racemase by searching the nucleotide sequence information on *Pseudomonas putida* KT2440 (ATCC 47054) whose genomic DNA sequence had been partly disclosed. They have further revealed that the gene product and a gene product derived from *Pseudomonas putida* IFO12996 which shows a high homology to said gene product actually have low-substrate-specific amino acid racemase activity, and have obtained the DNA, which has led to the completion of the present invention.

That is, the present invention relates to the following (1) to (13).

(1) A protein consisting of the amino acid sequence shown in SEQ ID NO: 1.

(2) A protein consisting of an amino acid sequence wherein one or more amino acid residues are deleted, substituted or added in the amino acid sequence shown in SEQ ID NO: 1 and having low-substrate-specific amino acid racemase activity.

(3) A DNA encoding the protein according to the above (1) or (2).

(4) A DNA consisting of the nucleotide sequence shown in SEQ ID NO: 3 or 4.

(5) A DNA hybridizing with DNA consisting of a nucleotide sequence complementary to the nucleotide sequence shown in SEQ ID NO: 3 or 4 under stringent conditions and encoding a protein having low-substrate-specific amino acid racemase activity.

(6) A recombinant DNA comprising the DNA according to any of the above (3) to (5).

(7) A transformant carrying the recombinant DNA according to the above (6).

(8) The transformant according to the above (7), which is obtained by using a microorganism, a plant cell, an insect cell or an animal cell as the host cell.

(9) The transformant according to the above (8), wherein the microorganism is a microorganism belonging to the genus *Escherichia*.

(10) A process for producing a protein having low-substrate-specific amino acid racemase activity, which comprises culturing the transformant according to any of the above (7) to (9) in a medium, allowing the protein to form and accumulate in the culture, and recovering the protein from the culture.

(11) A process for producing a racemic amino acid, which comprises allowing a culture of the transformant according to any of the above (7) to (9) or a treated matter thereof as an enzyme source and an amino acid to be present in an aqueous medium to racemize the amino acid in the aqueous medium, and recovering the racemic amino acid from the aqueous medium.

(12) The process according to the above (11), wherein the treated matter of the culture is concentrated culture, dried culture, cells obtained by centrifuging the culture, a product obtained by subjecting the cells to drying, freeze-drying, treatment with a surfactant, ultrasonication, mechanical friction, treatment with a solvent, enzymatic treatment, protein fractionation or immobilization, or an enzyme preparation obtained by extracting the cells.

(13) The process according to the above (11), wherein the amino acid to be racemized is selected from the group consisting of lysine, arginine, ornithine, methionine, serine, norvaline, alanine, asparagine, leucine, histidine, aspartic acid, threonine, glutamine and 2-aminobutyric acid.

The present invention is described in detail below.

The proteins of the present invention are proteins having low-substrate-specific amino acid racemase activity derived from *Pseudomonas putida*. Specific examples of such proteins are a protein having the amino acid sequence shown in SEQ ID NO: 1, and a protein consisting of an amino acid sequence wherein one or more amino acid residues are deleted, substituted or added in the amino acid sequence shown in SEQ ID NO: 1 and having low-substrate-specific amino acid racemase activity.

The protein consisting of an amino acid sequence wherein one or more amino acid residues are deleted, substituted or added and having low-substrate-specific amino acid racemase activity can be obtained, for example, by introducing a site-directed mutation into DNA encoding a protein having the amino acid sequence shown in SEQ ID NO: 1 by site-directed mutagenesis described in Molecular Cloning, A Laboratory Manual, Third Edition, Cold Spring Harbor Laboratory Press (2001) (hereinafter abbreviated as Molecular Cloning, Third Edition); Current Protocols in Molecular Biology, John Wiley & Sons (1987–1997) (hereinafter abbreviated as Current Protocols in Molecular Biology); Nucleic Acids Research, 10, 6487 (1982); Proc. Natl. Acad. Sci. USA, 79, 6409 (1982); Gene, 34, 315 (1985); Nucleic Acids Research, 13, 4431 (1985); Proc. Natl. Acad. Sci. USA, 82, 488 (1985), etc.

The number of amino acid residues which are deleted, substituted or added is not specifically limited, but is within the range where deletion, substitution or addition is possible by known methods such as the above site-directed mutagenesis. The suitable number is 1 to dozens, preferably 1 to 20, more preferably 1 to 10, further preferably 1 to 5.

The expression "one or more amino acid residues are deleted, substituted or added in the amino acid sequence shown in SEQ ID NO: 1" means that the amino acid sequence contains deletion, substitution or addition of a single or plural amino acid residues at an arbitrary position therein. Deletion, substitution and addition may be simultaneously contained in one sequence, and amino acid residues to be substituted or added may be either natural or not. Examples of the natural amino acid residues are L-alanine, L-asparagine, L-aspartic acid, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine and L-cysteine.

The following are examples of the amino acid residues capable of mutual substitution. The amino acid residues in the same group can be mutually substituted.

Group A: leucine, isoleucine, norleucine, valine, norvaline, alanine, 2-aminobutanoic acid, methionine, O-methylserine, t-butylglycine, t-butylalanine, cyclohexylalanine Group B: aspartic acid, glutamic acid, isoaspartic acid, isoglutamic acid, 2-aminoadipic acid, 2-aminosuberic acid Group C: asparagine, glutamine Group D: lysine, arginine, ornithine, 2,4-diaminobutanoic acid, 2,3-diaminopropionic acid Group E: proline, 3-hydroxyproline, 4-hydroxyproline Group F: serine, threonine, homoserine Group G: phenylalanine, tyrosine In order that the protein having an amino acid sequence wherein one or more amino acid residues are deleted, substituted or added in the amino acid sequence shown in SEQ ID NO: 1 may have low-substrate-specific amino acid racemase activity, it is desirable that the homology of its amino acid sequence to the amino acid sequence shown in SEQ ID NO: 1 is 60% or more, usually 80% or more, particularly 95% or more.

The homology among amino acid sequences and nucleotide sequences can be determined by using algorithm BLAST by Karlin and Altschul [Proc. Natl. Acad. Sci. USA, 90, 5873 (1993)] and FASTA [Methods Enzymol., 183, 63 (1990)]. On the basis of the algorithm BLAST, programs such as BLASTN and BLASTX have been developed [J. Mol. Biol., 215, 403 (1990)]. When a nucleotide sequence is analyzed by BLASTN on the basis of BLAST, the parameters, for instance, are as follows: score=100 and wordlength=12. When an amino acid sequence is analyzed by BLASTX on the basis of BLAST, the parameters, for instance, are as follows: score=50 and wordlength=3. When BLAST and Gapped BLAST programs are used, default parameters of each program are used. The specific techniques for these analyses are known (http://www.ncbi.nlm.nih.gov.).

The DNAs of the present invention include:

(1) DNA encoding a protein having the amino acid sequence shown in SEQ ID NO: 1;

(2) DNA encoding a protein consisting of an amino acid sequence wherein one or more amino acid residues are deleted, substituted or added in the amino acid sequence shown in SEQ ID NO: 1 and having low-substrate-specific amino acid racemase activity;

(3) DNA having the nucleotide sequence shown in SEQ ID NO: 3 or 4; and (4) DNA hybridizing with DNA consisting of a nucleotide sequence complementary to the nucleotide sequence shown in SEQ ID NO: 3 or 4 under stringent conditions and encoding a protein having low-substrate-specific amino acid racemase activity.

The above DNA capable of hybridization under stringent conditions refers to DNA which is obtained by colony hybridization, plaque hybridization, Southern blot hybridization or the like using a part or the whole of DNA consisting of a nucleotide sequence complementary to the nucleotide sequence shown in SEQ ID NO: 3 or 4 as a probe. A specific example of such DNA is DNA which can be identified by performing hybridization at 65° C. in the presence of 0.7 to 1.0 mmol/sodium chloride using a filter with colony- or plaque-derived DNA immobilized thereon, and then washing the filter at 65° C. with a 0.1 to 2-fold conc. SSC solution (1-fold conc. SSC solution: 150 mmol/l sodium chloride and 15 mmol/l sodium citrate). Hybridization can be carried out according to the methods described in Molecular Cloning, Third Edition; Current Protocols in Molecular Biology; DNA Cloning 1: Core Techniques, A Practical Approach, Second Edition, Oxford University (1995), etc.

An example of the above partial DNA is DNA consisting of arbitrary 10 to 50, preferably 15 to 50, more preferably 17 to 50 contiguous nucleotides in a nucleotide sequence complementary to the nucleotide sequence shown in SEQ ID NO: 3 or 4.

The hybridizable DNA is, for example, DNA having at least 60% homology, preferably 80% or more homology, more preferably 95% or more homology to the nucleotide sequence shown in SEQ ID NO: 3 or 4 as calculated using the above BLAST, FASTA, etc. based on the above parameters, etc.

1. Acquisition of the DNA of the Present Invention

The DNA of the present invention encoding a protein having low-substrate-specific amino acid racemase activity can be prepared from a microorganism belonging to the genus *Pseudomonas*. Examples of the microorganisms belonging to the genus *Pseudomonas* are those belonging to *Pseudomonas putida*, specifically, *Pseudomonas putida* ATCC 47054 and *Pseudomonas putida* IFO12296.

A microorganism belonging to *Pseudomonas putida* is cultured by a known method.

After the culturing, the chromosomal DNA of the microorganism is isolated and purified by a known method (e.g., Current Protocols in Molecular Biology).

The DNA of the present invention can be obtained by PCR [PCR Protocols, Academic Press (1990)] using primers designed based on the nucleotide sequence shown in SEQ ID NO: 3 or 4 and the chromosomal DNA isolated above as a template.

The DNA of the present invention can also be obtained by hybridization using the synthetic DNA designed based on the nucleotide sequence shown in SEQ ID NO: 3 or 4 as a probe.

Further, the DNA of the present invention can be obtained by chemical synthesis using a DNA synthesizer (Model 8905, PerSeptive Biosystems) based on the nucleotide sequence shown in SEQ ID NO: 3 or 4.

It can be confirmed that the obtained DNA is the desired DNA by inserting the obtained DNA, as such or after cleavage with appropriate restriction enzymes, into a vector by a conventional method, and determining its nucleotide sequence by a conventional sequencing method such as the dideoxy method [Proc. Natl. Acad. Sci. USA, 74, 5463 (1977)] or by using a nucleotide sequencer such as ABI PRISM 3700 DNA Sequencer (Applied Biosystems).

Examples of the DNAs that can be obtained by the above-described methods are DNAs having the nucleotide sequences shown in SEQ ID NOS: 3 and 4.

2. Preparation of the Recombinant DNA of the Present Invention

The recombinant DNA of the present invention can be obtained by inserting the DNA of the present invention obtained by the methods of 1 above into an appropriate vector.

Vectors suitable for the insertion of the DNA of the present invention include pBluescript II KS(+) (Stratagene), pDIRECT [Nucleic Acids Res., 18, 6069 (1990)], pCR-Script Amp SK(+) (Stratagene), pT7Blue (Novagen), pCR-Blunt (Invitrogen), pCR-TRAP (GenHunter), etc.

3. Preparation of the Transformant of the Present Invention

The transformant of the present invention can be obtained by introducing the recombinant DNA obtained in 2 above into an appropriate host cell. The host cells include microorganisms, plant cells, insect cells and animal cells.

An example of the transformant obtained using a microorganism as a host cell is *Escherichia coli* carrying a recombinant DNA comprising DNA having the sequence shown in SEQ ID NO: 3 or 4.

Examples of *Escherichia coli* are *Escherichia coli* DH5α, *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* MP347, *Escherichia coli* NM522 and *Escherichia coli* ME8415.

Introduction of the recombinant DNA can be carried out by any of the methods for introducing DNA into the above host cells, for example, the method using calcium ion [Proc. Natl. Acad. Sci. USA, 69, 2110 (1972)], the protoplast method (Japanese Published Unexamined Patent Application No. 248394/88) and electroporation [Nucleic Acids Res., 16, 6127 (1988)].

Specific examples of *Escherichia coli* carrying a recombinant DNA having DNA consisting of the nucleotide sequence shown in SEQ ID NO: 3 or 4 are *Escherichia coli* DH5α/pARkt1 and *Escherichia coli* DH5α/pARsd3.

4. Preparation of the Protein of the Present Invention

The protein of the present invention can be produced by expressing the DNA of the present invention which can be obtained by the methods of 1 above in host cells using the methods described in Molecular Cloning, Third Edition, Current Protocols in Molecular Biology, etc., for example, in the following manner.

On the basis of the DNA of the present invention, a DNA fragment of an appropriate length comprising a region encoding the protein is prepared according to need. The productivity of the protein can be improved by replacing a nucleotide in the nucleotide sequence of the region encoding the protein so as to make a codon most suitable for the expression in a host cell.

The DNA fragment is inserted downstream of a promoter in an appropriate expression vector to prepare a recombinant DNA.

Then, the recombinant DNA is introduced into a host cell suited for the expression vector, whereby a transformant which produces the protein of the present invention can be obtained.

As the host cell, any bacterial cells, yeast cells, animal cells, insect cells, plant cells, etc. that are capable of expressing the desired gene can be used.

The expression vectors that can be employed are those capable of autonomous replication or integration into the chromosome in the above host cells and comprising a promoter at a position appropriate for the transcription of the DNA of the present invention.

When a procaryote such as a bacterium is used as the host cell, it is preferred that the recombinant DNA comprising the DNA encoding the protein used in the production process of the present invention is a recombinant DNA which is capable of autonomous replication in the procaryote and which comprises a promoter, a ribosome binding sequence, the DNA of the present invention and a transcription termination sequence. The recombinant DNA may further comprise a gene regulating the promoter.

Examples of suitable expression vectors are pHelix1 (Roche Diagnostics), pKK233-2 (Amersham Pharmacia Biotech), pSE280 (Invitrogen), pGEMEX-1 (Promega), pQE-8 (Qiagen), pET-3 (Novagen), pCR-Blunt (Invitrogen), pKYP10 (Japanese Published Unexamined Patent Application No. 110600/83), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK(+), pBluescript II KS(-) (Stratagene), pTrS30 [prepared from *Escherichia coli* JM109/pTrS30 (FERM BP-5407)], pTrS32 [prepared from *Escherichia coli* JM109/pTrS32 (FERM BP-5408)], pPAC31 (WO98/12343), pUC19 [Gene, 33, 103 (1985)], pSTV28 (Takara Shuzo Co., Ltd.), pUC118 (Takara Shuzo Co., Ltd.) and pPA1 (Japanese Published Unexamined Patent Application No. 233798/88).

As the promoter, any promoters capable of functioning in host cells such as *Escherichia coli* can be used. For example, promoters derived from *Escherichia coli* or phage, such as trp promoter (Ptrp), lac promoter (Plac), $P_L$ promoter, $P_R$ promoter and $P_{SE}$ promoter, SPO1 promoter, SPO2 promoter and penP promoter can be used. Artificially designed and modified promoters such as a promoter in which two Ptrps are combined in tandem (Ptrp×2), tac promoter, lacT7 promoter and letI promoter, etc. can also be used.

It is preferred to use a plasmid in which the distance between the Shine-Dalgarno sequence (ribosome binding sequence) and the initiation codon is adjusted to an appropriate length (e.g., 6 to 18 nucleotides).

In the recombinant DNA of the present invention, the transcription termination sequence is not essential for the expression of the DNA of the present invention, but it is preferred to place the transcription termination sequence immediately downstream of the structural gene.

Examples of suitable procaryotes include microorganisms belonging to the genera *Escherichia*, *Serratia*, *Bacillus*,

*Brevibacterium, Corynebacterium, Microbacterium* and *Pseudomonas*. Specific examples of the above microorganisms are *Escherichia coli* DH5α, *Escherichia coli* XL1-Blue, *Escherichia coli* XL2-Blue, *Escherichia coli* DH1, *Escherichia coli* NM522, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Serratia ficaria, Serratia fonticola, Serratia liquefaciens, Serratia marcescens, Bacillus subtilis, Bacillus amyloliquefaciens, Brevibacterium immariophilum* ATCC 14068, *Brevibacterium saccharolyticum* ATCC 14066, *Corynebacterium ammoniagenes, Corynebacterium glutamicum* ATCC 13032, *Corynebacterium glutamicum* ATCC 14067, *Corynebacterium glutamicum* ATCC 13869, *Corynebacterium acetoacidophilum* ATCC 13870, *Microbacterium ammoniaphilum* ATCC 15354 and *Pseudomonas* sp. D-0110.

Introduction of the recombinant DNA can be carried out by any of the methods for introducing DNA into the above host cells, for example, the method using calcium ion [Proc. Natl. Acad. Sci. USA, 69, 2110 (1972)], the protoplast method (Japanese Published Unexamined Patent Application No. 248394/88) and electroporation [Nucleic Acids Res., 16, 6127 (1988)].

When a yeast strain is used as the host cell, YEp13 (ATCC 37115), YEp24 (ATCC 37051), YCp50 (ATCC 37419), pHS19, pHS15, etc. can be used as the expression vector.

As the promoter, any promoters capable of functioning in yeast strains can be used. Suitable promoters include PHO5 promoter, PGK promoter, GAP promoter, ADH promoter, gal 1 promoter, gal 10 promoter, heat shock polypeptide promoter, MFα1 promoter and CUP 1 promoter.

Examples of suitable host cells are yeast strains belonging to the genera *Saccharomyces, Schizosaccharomyces, Kluyveromyces, Trichosporon, Schwanniomyces, Pichia* and *Candida*, specifically, *Saccharomyces cerevisiae, Schizosaccharomyces pombe, Kluyveromyces lactis, Trichosporon pullulans, Schwanniomyces alluvius, Pichia pastoris* and *Candida utilis*.

Introduction of the recombinant DNA can be carried out by any of the methods for introducing DNA into yeast, for example, electroporation [Methods in Enzymology, 194, 182 (1990)], the spheroplast method [Proc. Natl. Acad. Sci. USA, 81, 4889 (1984)] and the lithium acetate method [J. Bacteriol., 153, 163 (1983)].

When an animal cell is used as the host cell, pcDNAI, pcDM8 (Invitrogen), pAGE107 (Japanese Published Unexamined Patent Application No. 22979/91), pAS3-3 (Japanese Published Unexamined Patent Application No. 227075/90), pcDNAI/Amp (Invitrogen), pREP4 (Invitrogen), pAGE103 [J. Biochem., 101, 1307 (1987)], pAGE210, etc. can be used as the expression vector.

As the promoter, any promoters capable of functioning in animal cells can be used. Suitable promoters include the promoter of IE (immediate early) gene of cytomegalovirus (CMV), SV40 early promoter, metallothionein promoter, the promoter of a retrovirus, heat shock promoter, SRα promoter, etc. The enhancer of IE gene of human CMV may be used in combination with the promoter.

Examples of suitable host cells are mouse myeloma cells, rat myeloma cells, mouse hybridomas, human-derived Namalwa cells, human embryonic kidney cells, human leukemia cells, African green monkey kidney cells, Chinese hamster-derived CHO cells, and HBT5637 (Japanese Published Unexamined Patent Application No. 299/88).

The mouse myeloma cells include SP2/0 and NSO; the rat myeloma cells include YB2/0; the human embryonic kidney cells include HEK293 (ATCC: CRL-1573); the human leukemia cells include BALL-1; and the African green monkey kidney cells include COS-1 and COS-7.

Introduction of the recombinant DNA can be carried out by any of the methods for introducing DNA into animal cells, for example, electroporation [Cytotechnology, 3, 133 (1990)], the calcium phosphate method (Japanese Published Unexamined Patent Application No. 227075/90), lipofection [Proc. Natl. Acad. Sci. USA, 84, 7413 (1987)], and the method described in Virology, 52, 456 (1973).

When an insect cell is used as the host cell, the protein can be expressed by using the methods described in Baculovirus Expression Vectors, A Laboratory Manual, W. H. Freeman and Company, New York (1992); Current Protocols in Molecular Biology; Molecular Biology, A Laboratory Manual; Bio/Technology, 6, 47 (1988), etc.

That is, the recombinant gene transfer vector and a baculovirus are cotransfected into insect cells to obtain a recombinant virus in the culture supernatant of the insect cells, and then insect cells are infected with the recombinant virus, whereby the protein can be expressed.

Examples of the gene transfer vectors suitable for use in this method are pVL1392, pVL1393 and pBlueBacIII (products of Invitrogen).

An example of the baculovirus is *Autographa californica* nuclear polyhedrosis virus, which is a virus infecting insects belonging to the family Barathra.

Examples of the insect cells are ovarian cells of *Spodoptera frugiperda*, ovarian cells of *Trichoplusia ni*, and cultured cells derived from silkworm ovary.

The ovarian cells of *Spodoptera frugiperda* include Sf9 and Sf21 (Baculovirus Expression Vectors, A Laboratory Manual); the ovarian cells of *Trichoplusia ni* include High 5 and BTI-TN-5B1–4 (Invitrogen); and the cultured cells derived from silkworm ovary include *Bombyx mori* N4.

Cotransfection of the above recombinant gene transfer vector and the above baculovirus into insect cells for the preparation of the recombinant virus can be carried out by the calcium phosphate method (Japanese Published Unexamined Patent Application No. 227075/90), lipofection [Proc. Natl. Acad. Sci. USA, 84, 7413 (1987)], etc.

When a plant cell is used as the host cell, Ti plasmid, tobacco mosaic virus vector, etc. can be used as the expression vector.

As the promoter, any promoters capable of functioning in plant cells can be used. Suitable promoters include 35S promoter of cauliflower mosaic virus (CaMV), rice actin 1 promoter, etc.

Examples of suitable host cells are cells of plants such as tobacco, potato, tomato, carrot, soybean, rape, alfalfa, rice, wheat and barley.

Introduction of the recombinant vector can be carried out by any of the methods for introducing DNA into plant cells, for example, the method using *Agrobacterium* (Japanese Published Unexamined Patent Application Nos. 140885/84 and 70080/85, WO94/00977), electroporation (Japanese Published Unexamined Patent Application No. 251887/85) and the method using particle gun (gene gun) (Japanese Patent Nos. 2606856 and 2517813).

The protein of the present invention can be produced by culturing the transformant obtained as above in a medium, allowing the protein of the present invention to form and accumulate in the culture, and recovering the protein from the culture.

Culturing of the transformant of the present invention in a medium can be carried out according to conventional methods for culturing the host.

For the culturing of the transformant obtained by using a procaryote such as *Escherichia coli* or a eucaryote such as yeast as the host, any of natural media and synthetic media can be used insofar as it is a medium suitable for efficient culturing of the transformant which contains carbon sources, nitrogen sources, inorganic salts, etc. which can be assimilated by the host used.

As the carbon sources, any carbon sources that can be assimilated by the host can be used. Examples of suitable carbon sources include carbohydrates such as glucose, fructose, sucrose, molasses containing them, starch and starch hydrolyzate; organic acids such as acetic acid and propionic acid; and alcohols such as ethanol and propanol.

Examples of the nitrogen sources include ammonia, ammonium salts of organic or inorganic acids such as ammonium chloride, ammonium sulfate, ammonium acetate and ammonium phosphate, peptone, meat extract, yeast extract, corn steep liquor, casein hydrolyzate, soybean cake, soybean cake hydrolyzate, and various fermented microbial cells and digested products thereof.

Examples of the inorganic salts include potassium dihydrogenphosphate, dipotassium hydrogenphosphate, magnesium phosphate, magnesium sulfate, sodium chloride, ferrous sulfate, manganese sulfate, copper sulfate and calcium carbonate.

Culturing is usually carried out under aerobic conditions, for example, by shaking culture or submerged spinner culture under aeration. The culturing temperature is preferably 15 to 40° C., and the culturing period is usually 5 hours to 7 days. The pH is maintained at 3.0 to 9.0 during the culturing. The pH adjustment is carried out by using an organic or inorganic acid, an alkali solution, urea, calcium carbonate, ammonia, etc.

If necessary, antibiotics such as ampicillin and tetracycline may be added to the medium during the culturing.

When a microorganism transformed with an expression vector comprising an inducible promoter is cultured, an inducer may be added to the medium, if necessary. For example, in the case of a microorganism transformed with an expression vector comprising lac promoter, isopropyl-β-D-thiogalactopyranoside or the like may be added to the medium; and in the case of a microorganism transformed with an expression vector comprising trp promoter, indoleacrylic acid or the like may be added.

For the culturing of the transformant obtained by using an animal cell as the host cell, generally employed media such as RPMI1640 medium [J. Am. Med. Assoc., 199, 519 (1967)], Eagle's MEM [Science, 122, 501 (1952)], DMEM [Virology, 8, 396 (1959)] and 199 medium [Proc. Soc. Biol. Med., 73, 1 (1950)], media prepared by adding fetal calf serum or the like to these media, etc. can be used as the medium.

Culturing is usually carried out at pH 6 to 8 at 25 to 40° C. for 1 to 7 days in the presence of 5% $CO_2$.

If necessary, antibiotics such as kanamycin, penicillin and streptomycin may be added to the medium during the culturing.

For the culturing of the transformant obtained by using an insect cell as the host cell, generally employed media such as TNM-FH medium (PharMingen), Sf-900 II SFM medium (Life Technologies, Inc.), ExCell 400 and ExCell 405 (JRH Biosciences) and Grace's Insect Medium [Nature, 195, 788 (1962)] can be used as the medium.

Culturing is usually carried out at pH 6 to 7 at 25 to 30° C. for 1 to 5 days.

If necessary, antibiotics such as gentamicin may be added to the medium during the culturing.

The transformant obtained by using a plant cell as the host cell may be cultured in the form of cells as such or after differentiation into plant cells or plant organs. For the culturing of such transformant, generally employed media such as Murashige-Skoog (MS) medium and White medium, media prepared by adding phytohormones such as auxin and cytokinin to these media, etc. can be used as the medium.

Culturing is usually carried out at pH 5 to 9 at 20 to 40° C. for 3 to 60 days.

If necessary, antibiotics such as kanamycin and hygromycin may be added to the medium during the culturing.

As described above, the protein of the present invention can be produced by culturing the transformant derived from a microorganism, an animal cell, an insect cell or a plant cell and carrying the recombinant DNA comprising the DNA encoding the protein according to a conventional culturing method, allowing the protein to form and accumulate, and recovering the protein from the culture.

When the protein is expressed using yeast, an animal cell, an insect cell or a plant cell, a glycosylated protein can be obtained.

The protein of the present invention may be produced by intracellular production by host cells, extracellular secretion by host cells or production on outer membranes by host cells. A desirable production method can be adopted by changing the kind of the host cells used or the structure of the protein to be produced.

When the protein of the present invention is produced in host cells or on outer membranes of host cells, it is possible to force the protein to be secreted outside the host cells by applying the method of Paulson, et al. [J. Biol. Chem., 264, 17619 (1989)], the method of Lowe, et al. [Proc. Natl. Acad. Sci. USA, 86, 8227 (1989); Genes Develop., 4, 1288 (1990)], or the methods described in Japanese Published Unexamined Patent Application No. 336963/93, WO94/23021, etc.

That is, extracellular secretion of the protein of the present invention by host cells can be caused by expressing it in the form of a protein in which a signal peptide is added upstream of a protein containing the active site of the protein of the present invention by the use of recombinant DNA techniques.

It is also possible to increase the protein production by utilizing a gene amplification system using a dihydrofolate reductase gene or the like according to the method described in Japanese Published Unexamined Patent Application No. 227075/90.

Further, the protein of the present invention can be produced using an animal having an introduced gene (non-human transgenic animal) or a plant having an introduced gene (transgenic plant) constructed by redifferentiation of animal or plant cells carrying the introduced gene.

When the transformant is an animal or plant, the protein can be produced by raising or culturing the animal or plant in a usual manner, allowing the protein to form and accumulate therein, and recovering the protein from the animal or plant.

Production of the protein of the present invention using an animal can be carried out, for example, by producing the protein in an animal constructed by introducing the gene according to known methods [Am. J. Clin. Nutr., 63, 639S (1996); Am. J. Clin. Nutr., 63, 627S (1996); Bio/Technology, 9, 830 (1991)].

In the case of an animal, the protein used in the production process of the present invention can be produced, for example, by raising a non-human transgenic animal carrying the introduced DNA encoding the protein, allowing the protein to form and accumulate in the animal, and recovering the protein from the animal. The places where the protein is formed and accumulated include milk (Japanese Published Unexamined Patent Application No. 309192/88), egg, etc. of the animal. As the promoter in this process, any promoters capable of functioning in an animal can be used. Preferred promoters include mammary gland cell-specific promoters such as a casein promoter, β casein promoter, β lactoglobulin promoter and whey acidic protein promoter.

Production of the protein used in the production process of the present invention using a plant can be carried out, for example, by culturing a transgenic plant carrying the introduced DNA encoding the protein of the present invention according to known methods [Soshiki Baiyo (Tissue Culture), 20, (1994); Soshiki Baiyo, 21, (1995); Trends Biotechnol., 15, 45 (1997)], allowing the protein to form and accumulate in the plant, and recovering the protein from the plant.

The protein produced by the transformant used in the production process of the present invention can be isolated and purified by conventional methods for isolating and purifying enzymes.

For example, when the protein used in the production process of the present invention is expressed in a soluble form in cells, the cells are recovered by centrifugation after the completion of culturing and suspended in an aqueous buffer, followed by disruption using a sonicator, French press, Manton Gaulin homogenizer, Dynomill or the like to obtain a cell-free extract.

A purified protein preparation can be obtained by centrifuging the cell-free extract to obtain the supernatant and then subjecting the supernatant to ordinary means for isolating and purifying enzymes, e.g., extraction with a solvent, salting-out with ammonium sulfate, etc., desalting, precipitation with an organic solvent, anion exchange chromatography using resins such as diethylaminoethyl (DEAE)-Sepharose and DIAION HPA-75 (Mitsubishi Chemical Corporation), cation exchange chromatography using resins such as S-Sepharose FF (Pharmacia), hydrophobic chromatography using resins such as butyl Sepharose and phenyl Sepharose, gel filtration using a molecular sieve, affinity chromatography, chromatofocusing, and electrophoresis such as isoelectric focusing, alone or in combination.

When the protein is expressed as an inclusion body in cells, the cells are similarly recovered and disrupted, followed by centrifugation to obtain a precipitate fraction. After the protein is recovered from the precipitate fraction by an ordinary method, the inclusion body of the protein is solubilized with a protein-denaturing agent.

The solubilized protein solution is diluted with or dialyzed against a solution containing no protein-denaturing agent or a solution containing the protein-denaturing agent at such a low concentration that denaturation of protein is not caused, whereby the protein is renatured to have normal higher-order structure. Then, a purified protein preparation can be obtained by the same isolation and purification steps as described above.

When the protein used in the production process of the present invention or its derivative such as a glycosylated form is extracellularly secreted, the protein or its derivative such as a glycosylated form can be recovered in the culture supernatant.

That is, the culture is treated by the same means as above, e.g., centrifugation, to obtain a soluble fraction. A purified protein preparation can be obtained from the soluble fraction by using the same isolation and purification methods as described above.

An example of the protein obtained in the above manner is a protein having the amino acid sequence shown in SEQ ID NO: 1.

It is also possible to produce the protein used in the production process of the present invention as a fusion protein with another protein and to purify it by affinity chromatography using a substance having affinity for the fused protein. For example, according to the method of Lowe, et al. [Proc. Natl. Acad. Sci. USA, 86, 8227 (1989); Genes Develop., 4, 1288 (1990)] and the methods described in Japanese Published Unexamined Patent Application No. 336963/93 and WO94/23021, the polypeptide of the present invention can be produced as a fusion protein with protein A and can be purified by affinity chromatography using immunoglobulin G.

Further, it is possible to produce the protein used in the production process of the present invention as a fusion protein with a Flag peptide and to purify it by affinity chromatography using anti-Flag antibody [Proc. Natl. Acad. Sci. USA, 86, 8227 (1989); Genes Develop., 4, 1288 (1990)]. The polypeptide can also be purified by affinity chromatography using an antibody against said polypeptide.

The protein of the present invention can also be produced by chemical synthetic methods such as the Fmoc method (the fluorenylmethyloxycarbonyl method) and the tBoc method (the t-butyloxycarbonyl method) based on the amino acid information on the protein obtained above. Further, the protein can be chemically synthesized by using peptide synthesizers from Advanced ChemTech, Perkin-Elmer, Pharmacia, Protein Technology Instrument, Synthecell-Vega, PerSeptive, Shimadzu Corporation, etc.

3. Process for Production of a Racemic Amino Acid

There is no specific restriction as to the transformant used in the process for producing a racemic amino acid of the present invention insofar as it produces a protein having low-substrate-specific amino acid racemase activity. The transformant preferably produces a protein having low-substrate-specific amino acid racemase activity derived from a microorganism, more preferably the protein derived from a microorganism belonging to the genus *Pseudomonas*, further preferably the protein derived from *Pseudomonas putida*. Particularly preferred is the transformant producing the protein of the present invention described in 3 above.

The transformant which produces the protein having low-substrate-specific amino acid racemase activity can be obtained by isolating DNA encoding the protein having low-substrate-specific amino acid racemase activity from the chromosomal DNA of various organisms having low-substrate-specific amino acid racemase activity, preferably a microorganism, more preferably a microorganism belonging to the genus *Pseudomonas*, further preferably *Pseudomonas putida*, by PCR using primer DNAs designed based on the nucleotide sequence of the DNA of the present invention or hybridization using a part or the whole of the DNA of the present invention as a probe according to known methods, and then transforming a host cell using the DNA.

A racemic amino acid can be produced by allowing a culture of the above transformant of the present invention or a treated matter thereof as an enzyme source and an amino acid to be present in an aqueous medium to racemize the amino acid in the aqueous medium, and recovering the racemic amino acid from the aqueous medium.

The treated matters of the culture include concentrated culture, dried culture, cells obtained by centrifuging the culture, products obtained by treating the cells by various means such as drying, freeze-drying, treatment with a surfactant, ultrasonication, mechanical friction, treatment with a solvent, enzymatic treatment, protein fractionation and immobilization, an enzyme preparation obtained by extracting the cells, etc.

In the racemization of amino acids, the enzyme source is used at a concentration of 1 mU/l to 1000 U/l, preferably 10 mU/l to 100 U/l, one unit (U) being defined as the activity which forms 1 mmol of a D-amino acid from an optically pure L-amino acid at 30° C. in one minute.

As the amino acid used as a substrate, any L- or D-amino acids can be used. Suitable amino acids include alanine, glutamine, glutamic acid, valine, leucine, isoleucine, proline, phenylalanine, tryptophan, methionine, serine, threonine, cysteine, asparagine, tyrosine, lysine, arginine, histidine, aspartic acid, 2-aminobutyric acid, azaserine, 4-hydroxyproline, 3-hydroxyproline and ornithine, preferably, alanine, leucine, methionine, serine, threonine, lysine, arginine, histidine, asparagine, aspartic acid, 2-aminobutyric acid and ornithine, more preferably, lysine, arginine, ornithine, methionine, serine, norvaline, alanine, asparagine, leucine, histidine, aspartic acid, threonine, glutamine and 2-aminobutyric acid, further preferably, lysine, arginine, ornithine, methionine, serine, norvaline, alanine, asparagine, leucine, histidine, aspartic acid and threonine.

The amino acid as a substrate can be used at a concentration of 0.1 to 1000 g/l, preferably 0.5 to 800 g/l, more preferably 1 g/l to 500 g/l.

Aqueous media useful in the racemization of amino acids include water, buffers such as phosphate buffer, carbonate buffer, acetate buffer, borate buffer, citrate buffer and Tris buffer, alcohols such as methanol and ethanol, esters such as ethyl acetate, ketones such as acetone, amides such as acetamide, etc. The culture of the microorganism used as the enzyme source can be used also as the aqueous medium.

If necessary, a surfactant or an organic solvent may be added in the racemization of amino acids. Any surfactant that promotes the racemization of amino acids can be used. Suitable surfactants include nonionic surfactants such as polyoxyethylene octadecylamine (e.g., Nymeen S-215, NOF Corporation), cationic surfactants such as cetyltrimethylammonium bromide and alkyldimethylbenzylammonium chloride (e.g., Cation F2-40E, NOF Corporation), anionic surfactants such as lauroyl sarcosinate, and tertiary amines such as alkyldimethylamine (e.g., Tertiary Amine FB, NOF Corporation), which may be used alone or in combination. The surfactant is usually used at a concentration of 0.1 to 50 g/l. As the organic solvent, xylene, toluene, aliphatic alcohols, acetone, ethyl acetate, etc. may be used usually at a concentration of 0.1 to 50 ml/l.

The racemization of amino acids is carried out in the aqueous medium at pH 5 to 10, preferably pH 7 to 9, at 20 to 50° C. for 1 to 96 hours.

Determination of D- and L-amino acids in the reaction solution can be carried out by HPLC using a column [CROWNPAK-CR(+), Daicel Chemical Industries, Ltd.], etc.

Isolation and purification of DL-amino acid formed in the reaction solution can be carried out by ordinary methods for isolation and purification using active carbon, ion-exchange resins, etc.

Figure 1:
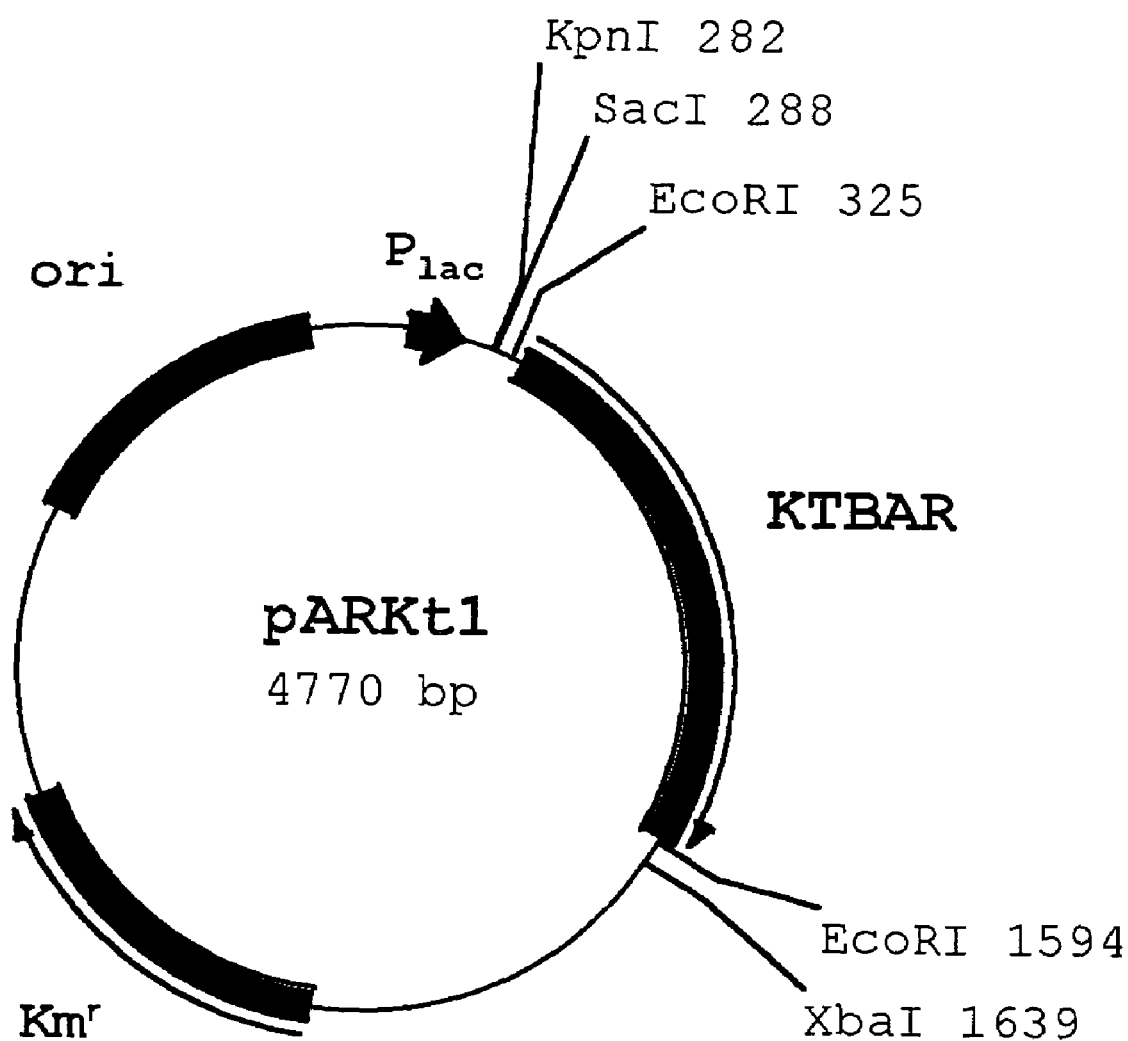
FIG. 1 shows the structure of plasmid pARkt1 expressing a low-substrate-specific amino acid racemase gene.

The symbols used in the drawings refer to the following.

Km$^r$: kanamycin resistance gene

Plac: lactose promoter

Ori: replication origin

KTBAR: low-substrate-specific amino acid racemase gene derived from *Pseudomonas putida* ATCC 47054

SDBAR: low-substrate-specific amino acid racemase gene derived from *Pseudomonas putida* IFO12296

Certain embodiments of the present invention are illustrated in the following examples. These examples are not to be construed as limiting the scope of the invention.

BEST MODES FOR CARRYING OUT THE INVENTION

EXAMPLE 1

Identification of a Low-Substrate-Specific Amino Acid Racemase Gene Utilizing Genomic DNA Nucleotide Sequence Database of *Pseudomonas putida* KT2440 (ATCC 47054)

A homology search was performed against the genomic DNA nucleotide sequence database of *Pseudomonas putida* KT2440 (ATCC 47054) [http://www.ncbi.nlm.nih.gov/Microb#blast/unfinishedgenome.html] using, as a query, the amino acid sequence shown in SEQ ID NO: 5, which is an internal amino acid sequence of low-substrate-specific amino acid racemase of *Pseudomonas putida* IFO12296, and using program TBLASTN 2.1.1.

As the result, the DNA consisting of the nucleotide sequence shown in SEQ ID NO: 3 was identified as an open reading frame encoding a protein containing the amino acid sequence wherein 13 amino acids were identical to those of the 14-amino acid sequence shown in SEQ ID NO: 5.

EXAMPLE 2

Construction of a Transformant which Expresses the Low-Substrate-Specific Amino Acid Racemase Gene Derived from *Pseudomonas putida* KT2440 (ATCC 47054)

*Pseudomonas putida* KT2440 (ATTC 47054) was cultured using an ordinary bouillon medium (Kyokuto Pharmaceutical Industrial Co., Ltd.) at 30° C. for 24 hours, and the culture was centrifuged to obtain cells.

The chromosomal DNA of the microorganism was isolated and purified from the cells by the method described in Current Protocols in Molecular Biology.

On the basis of the nucleotide sequence assumed to be the low-substrate-specific amino acid racemase gene of *Pseudomonas putida* identified in Example 1, a set of primer DNAs having the nucleotide sequences shown in SEQ ID NOS: 6 and 7 were synthesized using a DNA synthesizer (Model 8905, PerSeptive Biosystems).

The DNA fragment assumed to be the low-substrate-specific amino acid racemase gene of *Pseudomonas putida* KT2440 (ATCC 47054) in Example 1 was amplified in the following manner.

That is, PCR was carried out using the DNAs having the nucleotide sequences shown in SEQ ID NOS: 6 and 7 as a set of primers and the chromosomal DNA of *Pseudomonas putida* KT2440 (ATCC 47054) as a template. PCR was carried out by 30 cycles, one cycle consisting of reaction at 96° C. for 5 seconds, reaction at 58° C. for 30 seconds and reaction at 72° C. for one minute, using 50 µl of a reaction mixture comprising 0.1 µg of the chromosomal DNA, 0.5 µmol/l each of the primer DNAs, 2.5 units of Pyrobest DNA polymerase (Takara Shuzo Co., Ltd.), 5 µl of buffer for Pyrobest DNA polymerase (10×) and 200 µmol/l each of deoxy NTPs.

One-tenth of the resulting reaction mixture was subjected to agarose gel electrophoresis to confirm that the desired fragment was amplified. Then, the remaining reaction mixture was mixed with an equal amount of phenol/chloroform (1 vol/1 vol) saturated with TE [10 mmol/l Tris-HCl, 1 mmol/l EDTA (pH 8.0)].

The resulting mixture was centrifuged, and the obtained upper layer was mixed with a two-fold volume of cold ethanol and allowed to stand at −80° C. for 30 minutes. The resulting solution was centrifuged, and the obtained DNA was dissolved in 20 µl of TE buffer.

The obtained DNA solution (5 µl) was subjected to ligation reaction using pCR-Blunt vector (Invitrogen) and a ligation kit attached to the vector at 16° C. for one hour.

*Escherichia coli* DH5α was transformed using the ligation reaction mixture according to the above known method, spread on LB agar medium [10 g/l tryptone peptone (Difco), 10 g/l yeast extract (Difco), 5 g/l sodium chloride and 15 g/l agar] containing 50 µg/ml kanamycin, and cultured overnight at 30° C.

A plasmid was extracted from a colony of the transformant that grew on the medium according to the method described in Molecular Biology, Third Edition to obtain expression plasmid pARkt1. By using the plasmid, the nucleotide sequence of the DNA fragment amplified by the above PCR was determined, whereby it was confirmed that the DNA having the nucleotide sequence shown in SEQ ID NO: 3 and encoding a protein consisting of the amino acid sequence shown in SEQ ID NO: 1 was isolated, and the structure of the plasmid was also confirmed by restriction enzyme digestion (FIG. 1).

EXAMPLE 3

Construction of a Transformant Which Expresses the Low-Substrate-Specific Amino Acid Racemase Gene Derived from *Pseudomonas putida* IFO12296

*Pseudomonas putida* IFO12296 was cultured using an ordinary bouillon medium (Kyokuto Pharmaceutical Industrial Co., Ltd.) at 30° C. for 24 hours, and the culture was centrifuged to obtain cells.

The chromosomal DNA of the microorganism was isolated and purified from the cells by the method described in Current Protocols in Molecular Biology.

On the basis of the nucleotide sequence assumed to be the low-substrate-specific amino acid racemase gene of *Pseudomonas putida* KT2440 (ATCC 47054) specified in Example 1, a set of primer DNAs having the nucleotide sequences shown in SEQ ID NOS: 8 and 9 were synthesized using a DNA synthesizer (Model 8905, PerSeptive Biosystems).

A DNA fragment assumed to be the low-substrate-specific amino acid racemase gene was amplified from *Pseudomonas putida* IFO12296 which had been known to produce a protein having low-substrate-specific amino acid racemase activity in the following manner.

That is, PCR was carried out using a set of primer DNAs having the nucleotide sequences shown in SEQ ID NOS: 8 and 9 and the chromosomal DNA of *Pseudomonas putida* IFO12296 as a template. PCR was carried out by 30 cycles, one cycle consisting of reaction at 96° C. for 5 seconds, reaction at 58° C. for 30 seconds and reaction at 72° C. for one minute, using 50 µl of a reaction mixture comprising 0.1 µg of the chromosomal DNA, 0.5 µmol/l each of the primer DNAs, 2.5 units of Pyrobest DNA polymerase (Takara Shuzo Co., Ltd.), 5 µl of buffer for Pyrobest DNA polymerase (10×) and 200 µmol/l each of deoxy NTPs.

One-tenth of the resulting reaction mixture was subjected to agarose gel electrophoresis to confirm that the desired fragment was amplified. Then, the remaining reaction mixture was mixed with an equal amount of phenol/chloroform (1 vol/1 vol) saturated with TE.

The resulting mixture was centrifuged, and the obtained upper layer was mixed with a two-fold volume of cold ethanol and allowed to stand at −80° C. for 30 minutes. The resulting solution was centrifuged, and the obtained DNA was dissolved in 20 µl of TE.

The obtained DNA solution (5 µl) was subjected to ligation reaction using pCR-Blunt vector and a ligation kit attached to the vector at 16° C. for one hour.

*Escherichia coli* DH5α was transformed using the ligation reaction mixture according to the above known method, spread on LB agar medium containing 50 µg/ml kanamycin, and cultured overnight at 30° C.

Figure 2:
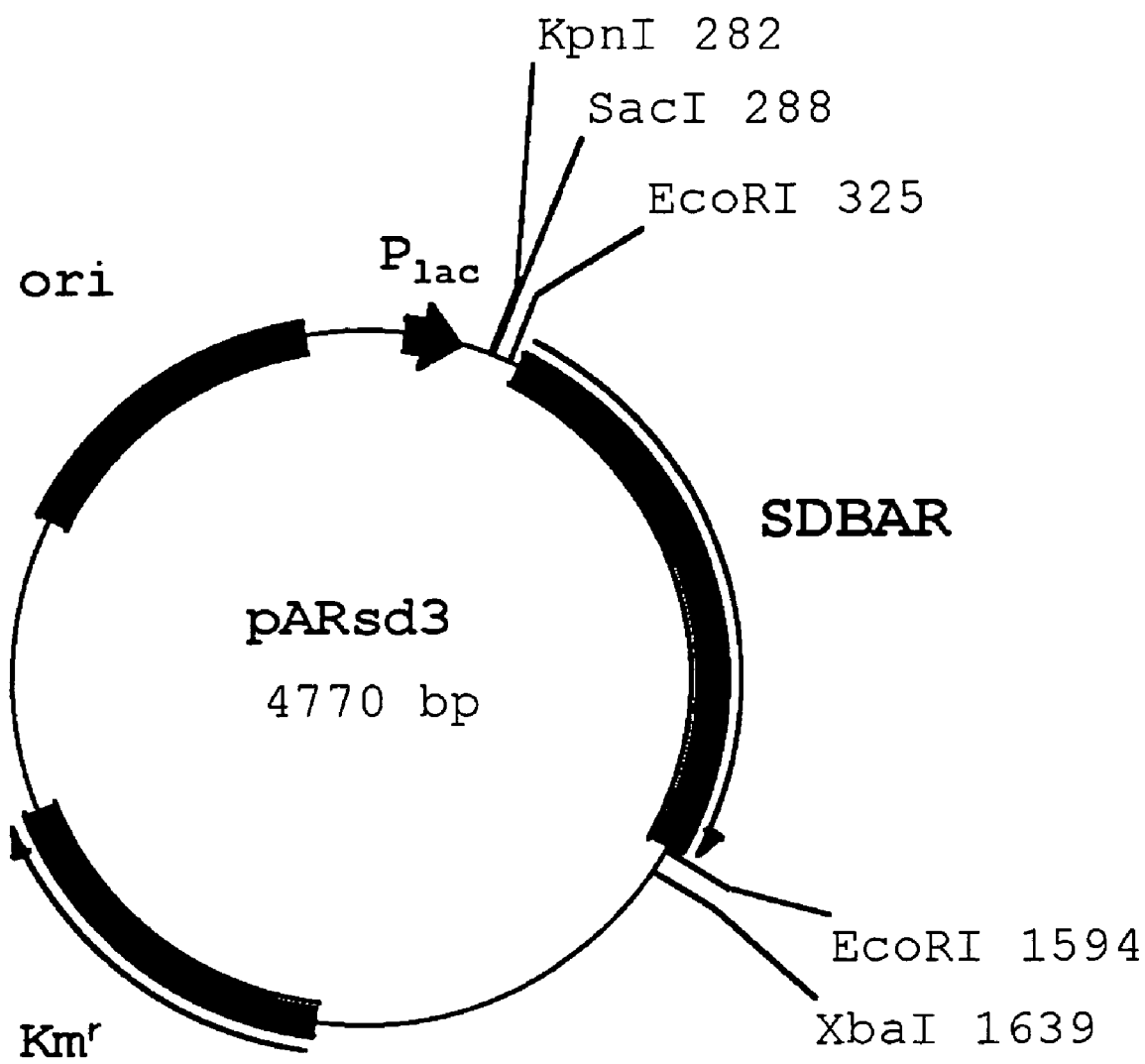
FIG. 2 shows the structure of plasmid pARsd3 expressing a low-substrate-specific amino acid racemase gene.

A plasmid was extracted from a colony of the transformant that grew on the medium according to the method described in Molecular Biology, Third Edition to obtain expression plasmid pARsd3. By using the plasmid, the nucleotide sequence of the DNA fragment amplified by the above PCR was determined, whereby it was confirmed that the DNA having the nucleotide sequence shown in SEQ ID NO: 4 and encoding a protein consisting of the amino acid sequence shown in SEQ ID NO: 2 was isolated, and the structure of the plasmid was also confirmed by restriction enzyme digestion (FIG. 2).

EXAMPLE 4

Examination of Substrate Specificity

*Escherichia coli* DH5α/pARkt1 and *Escherichia coli* DH5α/pARsd3 respectively obtained in Examples 2 and 3 were separately inoculated into 8 ml of LB medium containing 50 µg/ml kanamycin in a test tube, and cultured at 30° C. for 17 hours. Each culture was inoculated into 40 ml of LB medium containing 50 µg/ml kanamycin in a 300-ml Erlenmenyer flask in an amount of 5%, and cultured at 30° C. for 24 hours. The resulting culture was centrifuged to obtain wet cells. The wet cells could be stored at −20° C. according to need and could be used after thawing.

Reaction was carried out using the wet cells of the DH5α/pARkt1 strain or DH5α/pARsd3 strain as an enzyme source and the following reaction solution containing 50 mmol/l L-amino acid at 30° C. for one hour. The formed product was analyzed by HPLC under the following conditions. The results of the analysis are shown in Table 1.

| Composition of the reaction solution | |
|---|---|
| Wet cells | 1 g/l |
| L-amino acid | 50 mmol/l |
| Boric acid | 50 mmol/l (pH 8.5; adjusted with sodium hydroxide) |

Precolumn: CROWNPAK-CR(+) 5 µm 4.0×10 mm (Daicel Chemical Industries, Ltd.)
Column: CROWNPAK-CR(+) 5 µm 4.0×150 mm (Daicel Chemical Industries, Ltd.)
Mobile phase: H$_2$O (pH 1.0; adjusted with 60% perchloric acid)
Flow rate: 0.2 ml/min
Column temperature: 2° C.

TABLE 1

| Substrate | DH5 α/pARkt1 strain Product | | DH5 α/pARsd3 strain Product | |
|---|---|---|---|---|
| | D-form (mmol/l) | L-form (mmol/l) | D-form (mmol/l) | L-form (mmol/l) |
| L-lysine | 24.3 | 25.0 | 25.0 | 24.7 |
| L-arginine | 25.2 | 24.8 | 25.2 | 25.0 |
| L-ornithine | 14.8 | 35.1 | 24.9 | 25.1 |
| L-methionine | 24.6 | 24.9 | 24.5 | 25.5 |
| L-serine | 12.5 | 37.5 | 23.0 | 26.8 |
| L-norvaline | 15.7 | 34.2 | 23.0 | 27.3 |
| L-alanine | 9.8 | 40.0 | 18.6 | 30.9 |
| L-asparagine | 6.2 | 43.2 | 17.8 | 31.9 |
| L-leucine | 12.6 | 37.0 | 14.9 | 34.9 |
| L-histidine | 6.4 | 43.0 | 14.7 | 34.7 |
| L-aspartic acid | 0.3 | 49.7 | 0.8 | 48.2 |
| L-threonine | 1.1 | 48.5 | 0.7 | 48.5 |

INDUSTRIAL APPLICABILITY

The present invention enables the production of low-substrate-specific amino acid racemase in large amounts and the efficient racemization of various amino acids by using the enzyme.

SEQUENCE LISTING FREE TEXT

SEQ ID NO: 6—Description of artificial sequence: synthetic DNA

SEQ ID NO: 7—Description of artificial sequence: synthetic DNA

SEQ ID NO: 8—Description of artificial sequence: synthetic DNA

SEQ ID NO: 9—Description of artificial sequence: synthetic DNA

The invention claimed is:

1. An isolated DNA encoding a protein having an amino acid sequence which has at least 95% homology with the amino acid sequence shown in SEQ ID NO: 1 and having low-substrate-specific amino acid racemase activity.

2. An isolated DNA having the nucleotide sequence shown in SEQ ID NO: 3.

3. An isolated DNA which hybridizes with DNA consisting of a nucleotide sequence complementary to the nucleotide sequence shown in SEQ ID NO: 3 under the following conditions: hybridization in the presence of 0.7 to 1.0 mol/l sodium chloride at 65° C., and washing in a 0.1 to 2-fold conc. SSC solution at 65° C., and which encode a protein having low-substrate-specific amino acid racemase activity.

4. A recombinant DNA comprising the DNA according to claim 3.

5. An isolated transformed host cell harboring the recombinant DNA according to claim 4.

6. The transformed host cell according to claim 5, which is obtained by using a microorganism, a plant cell, an insect cell or an animal cell as the host cell.

7. The transformed host cell according to claim 6, wherein the microorganism is a microorganism belonging to the genus *Escherichia*.

8. A process for producing a protein having low-substrate-specific amino acid racemase activity, which comprises culturing the transformed host cell according to claim 5 in a medium, allowing the protein to form and accumulate in the culture, and recovering the protein from the culture.

9. A recombinant DNA comprising the DNA according to claim 2.

10. An isolated transformed host cell harboring the recombinant DNA according to claim 9.

11. A process for producing a protein having low-substrate-specific amino acid racemase activity, which comprises culturing the transformed host cell according to claim 10 in a medium, allowing the protein to form and accumulate in the culture, and recovering the protein from the culture.

12. A recombinant DNA comprising the DNA according to claim 1.

13. An isolated transformed host cell harboring the recombinant DNA according to claim 12.

14. A process for producing a protein having low-substrate-specific amino acid racemase activity, which comprises culturing the transformed host cell according to claim 13 in a medium, allowing the protein to form and accumulate in the culture, and recovering the protein from the culture.

15. An isolated DNA encoding the protein having the amino acid sequence shown in SEQ ID NO: 1.

16. A recombinant DNA comprising the DNA according to claim 15.

17. An isolated transformed host cell harboring the recombinant DNA according to claim 16.

18. A process for producing a protein having low-substrate-specific amino acid racemase activity, which comprises culturing the transformed host cell according to claim 17 in a medium, allowing the protein to form and accumulate in the culture, and recovering the protein from the culture.

* * * * *

```
                        SEQUENCE LISTING

<160> NUMBER OF SEQ ID NOS: 9

<210> SEQ ID NO 1
<211> LENGTH: 409
<212> TYPE: PRT
<213> ORGANISM: Pseudomonas putida ATCC 47054

<400> SEQUENCE: 1

Met Pro Phe Arg Arg Thr Leu Leu Ala Ala Ser Leu Ala Leu Leu Ile
 1               5                  10                  15

Thr Gly Gln Ala Pro Leu Tyr Ala Ala Pro Pro Leu Ser Met Asp Asn
             20                  25                  30

Gly Thr Asn Thr Leu Thr Val Gln Asn Ser Asn Ala Trp Val Glu Val
         35                  40                  45

Ser Ala Ser Ala Leu Gln His Asn Ile Arg Thr Leu Gln Ala Glu Leu
     50                  55                  60

Ala Gly Lys Ser Lys Leu Cys Ala Val Leu Lys Ala Asp Ala Tyr Gly
 65                  70                  75                  80

His Gly Ile Gly Leu Val Met Pro Ser Ile Ile Ala Gln Gly Val Pro
                 85                  90                  95

Cys Val Ala Val Ala Ser Asn Glu Glu Ala Arg Val Val Arg Ala Ser
                100                 105                 110

Gly Phe Thr Gly Gln Leu Val Arg Val Arg Leu Ala Ser Leu Ser Glu
            115                 120                 125
```

```
Leu Glu Asp Gly Leu Gln Tyr Asp Met Glu Glu Leu Val Gly Ser Ala
        130                 135                 140

Glu Phe Ala Arg Gln Ala Asp Ala Ile Ala Ala Arg His Gly Lys Thr
145                 150                 155                 160

Leu Arg Ile His Met Ala Leu Asn Ser Ser Gly Met Ser Arg Asn Gly
                165                 170                 175

Val Glu Met Ala Thr Trp Ser Gly Arg Gly Glu Ala Leu Gln Ile Thr
            180                 185                 190

Asp Gln Lys His Leu Lys Leu Val Ala Leu Met Thr His Phe Ala Val
        195                 200                 205

Glu Asp Lys Asp Val Arg Lys Gly Leu Ala Ala Phe Asn Glu Gln
210                 215                 220

Thr Asp Trp Leu Ile Lys His Ala Arg Leu Asp Arg Ser Lys Leu Thr
225                 230                 235                 240

Leu His Ala Ala Asn Ser Phe Ala Thr Leu Glu Val Pro Glu Ala Arg
                245                 250                 255

Leu Asp Met Val Arg Thr Gly Gly Ala Leu Phe Gly Asp Thr Val Pro
            260                 265                 270

Ala Arg Thr Glu Tyr Lys Arg Ala Met Gln Phe Lys Ser His Val Ala
        275                 280                 285

Ala Val His Ser Tyr Pro Ala Gly Asn Thr Val Gly Tyr Asp Arg Thr
        290                 295                 300

Phe Thr Leu Ala Arg Asp Ser Arg Leu Ala Asn Ile Thr Val Gly Tyr
305                 310                 315                 320

Ser Asp Gly Tyr Arg Arg Val Phe Thr Asn Lys Gly His Val Leu Ile
                325                 330                 335

Asn Gly His Arg Val Pro Val Val Gly Lys Val Ser Met Asn Thr Leu
            340                 345                 350

Met Val Asp Val Thr Asp Phe Pro Asp Val Lys Gly Gly Asn Glu Val
        355                 360                 365

Val Leu Phe Gly Lys Gln Ala Gly Gly Glu Ile Thr Gln Ala Glu Met
370                 375                 380

Glu Glu Ile Asn Gly Ala Leu Leu Ala Asp Leu Tyr Thr Val Trp Gly
385                 390                 395                 400

Asn Ser Asn Pro Lys Ile Leu Val Asp
                405

<210> SEQ ID NO 2
<211> LENGTH: 409
<212> TYPE: PRT
<213> ORGANISM: Pseudomonas putida IFO12296

<400> SEQUENCE: 2

Met Gln Phe Ser Arg Thr Leu Leu Ala Ala Ser Leu Ala Leu Leu Ile
1               5                   10                  15

Thr Gly Gln Ala Pro Leu Tyr Ala Ala Pro Leu Ser Met Asp Asn
            20                  25                  30

Gly Thr Thr Ala Leu Thr Ala Gln Asn Ser Asn Ala Trp Val Glu Ile
        35                  40                  45

Ser Ala Gly Ala Leu Gln His Asn Ile Arg Thr Leu Gln Ala Glu Leu
    50                  55                  60

Gly Gly Lys Ser Lys Leu Cys Ala Val Leu Lys Ala Asp Ala Tyr Gly
65                  70                  75                  80

His Gly Ile Gly Leu Val Met Pro Ser Ile Ile Ala Gln Gly Val Pro
                85                  90                  95
```

```
Cys Val Ala Val Ala Ser Asn Glu Glu Ala Arg Val Arg Ala Ser
            100                 105                 110

Gly Phe Thr Gly Gln Leu Val Arg Val Arg Leu Ala Ser Leu Gly Glu
            115                 120                 125

Val Glu Asp Ala Leu Gln Tyr Asp Met Glu Glu Leu Val Gly Ser Ala
            130                 135                 140

Glu Phe Ala Arg Gln Leu Asp Ala Ile Ala Glu Arg His Gly Lys Thr
145                 150                 155                 160

Leu Arg Ile His Met Ala Leu Asn Ser Ser Gly Met Ser Arg Asn Gly
                165                 170                 175

Val Glu Met Thr Thr Trp Ser Gly Arg Gly Glu Ala Leu Gln Ile Thr
            180                 185                 190

Asp Gln Lys His Leu Gln Leu Val Ala Leu Met Thr His Phe Ala Val
            195                 200                 205

Glu Asp Lys Asp Asp Val Arg Lys Gly Leu Ala Ala Phe Asn Glu Gln
            210                 215                 220

Thr Asp Trp Leu Ile Lys His Ala Lys Leu Asp Arg Ser Lys Leu Thr
225                 230                 235                 240

Leu His Ala Ala Asn Ser Phe Ala Thr Leu Glu Val Pro Glu Ala His
                245                 250                 255

Leu Asp Met Val Arg Thr Gly Gly Ala Leu Phe Gly Asp Thr Val Pro
            260                 265                 270

Thr Arg Thr Glu Tyr Gln Arg Val Met Gln Phe Lys Ser His Val Ala
            275                 280                 285

Ala Val His Ser Tyr Pro Ala Gly Asn Thr Val Gly Tyr Asp Arg Thr
            290                 295                 300

Phe Thr Leu Ala Arg Asp Ser Arg Leu Ala Asn Ile Thr Val Gly Tyr
305                 310                 315                 320

Ser Asp Gly Tyr Arg Arg Val Phe Thr Asn Lys Gly His Val Leu Ile
                325                 330                 335

Asn Gly His Arg Val Pro Val Val Gly Lys Val Ser Met Asn Thr Leu
            340                 345                 350

Met Val Asp Val Thr Asp Phe Pro Asp Val Lys Gly Gly Asn Glu Val
            355                 360                 365

Val Leu Phe Gly Lys Gln Ala Gly Arg Glu Ile Thr Gln Ala Glu Ile
            370                 375                 380

Glu Glu Ile Asn Gly Ala Leu Leu Ala Asp Leu Tyr Thr Val Trp Gly
385                 390                 395                 400

Ser Ser Asn Pro Lys Ile Leu Val Asp
                405
```

<210> SEQ ID NO 3
<211> LENGTH: 1227
<212> TYPE: DNA
<213> ORGANISM: Pseudomonas putida ATCC 47054

<400> SEQUENCE: 3

```
atg ccc ttt cgc cgt acc ctt ctg gct gca tcc ctg gca ctt ctg atc      48
Met Pro Phe Arg Arg Thr Leu Leu Ala Ala Ser Leu Ala Leu Leu Ile
 1               5                  10                  15 acc gga cag gcc ccc ctg tat gcg gca cca ccg ttg tcg atg gac aac      96
Thr Gly Gln Ala Pro Leu Tyr Ala Ala Pro Pro Leu Ser Met Asp Asn
             20                  25                  30 ggc acc aac acc ctg acc gtg caa aac agc aat gcc tgg gtc gaa gtc     144
Gly Thr Asn Thr Leu Thr Val Gln Asn Ser Asn Ala Trp Val Glu Val
```

-continued

|   | 35 | | | | 40 | | | | 45 | | | | | |
|---|---|---|---|---|---|---|---|---|---|---|---|---|---|---|

```
agc gcc agc gcc ctg cag cac aac atc cgc acg ctg cag gcc gag ctg      192
Ser Ala Ser Ala Leu Gln His Asn Ile Arg Thr Leu Gln Ala Glu Leu
 50              55                  60 gcc ggc aag tcc aag ctg tgc gcc gtg ctc aag gcc gat gcc tat ggc      240
Ala Gly Lys Ser Lys Leu Cys Ala Val Leu Lys Ala Asp Ala Tyr Gly
 65              70                  75                  80 cac ggt atc ggc ctg gta atg cca tcg atc atc gcc caa ggc gtg ccc      288
His Gly Ile Gly Leu Val Met Pro Ser Ile Ile Ala Gln Gly Val Pro
                 85                  90                  95 tgc gtg gcg gtg gcc agc aac gag gag gcc cgc gtg gtc cgc gcc agt      336
Cys Val Ala Val Ala Ser Asn Glu Glu Ala Arg Val Val Arg Ala Ser
            100                 105                 110 ggc ttc acc ggg caa ctg gtg cgg gta cgc ctg gcc agc ctc agc gag      384
Gly Phe Thr Gly Gln Leu Val Arg Val Arg Leu Ala Ser Leu Ser Glu
        115                 120                 125 ctg gaa gat ggc ttg cag tac gac atg gaa gag ctg gtg ggc agc gcg      432
Leu Glu Asp Gly Leu Gln Tyr Asp Met Glu Glu Leu Val Gly Ser Ala
130                 135                 140 gaa ttt gcc cgc cag gcc gat gcc atc gcc gcg cgc cat ggc aag acc      480
Glu Phe Ala Arg Gln Ala Asp Ala Ile Ala Ala Arg His Gly Lys Thr
145                 150                 155                 160 ttg cgc att cac atg gcg ctc aac tcc agc ggc atg agc cgc aac ggg      528
Leu Arg Ile His Met Ala Leu Asn Ser Ser Gly Met Ser Arg Asn Gly
                165                 170                 175 gtg gag atg gcc acc tgg tcc ggc cgt ggc gaa gcg ctg cag atc acc      576
Val Glu Met Ala Thr Trp Ser Gly Arg Gly Glu Ala Leu Gln Ile Thr
            180                 185                 190 gac cag aag cac ctc aag ctg gtc gcg ctg atg acc cac ttc gcc gtg      624
Asp Gln Lys His Leu Lys Leu Val Ala Leu Met Thr His Phe Ala Val
        195                 200                 205 gaa gac aag gac gat gta cgc aag ggc ctg gcg gca ttc aac gag cag      672
Glu Asp Lys Asp Asp Val Arg Lys Gly Leu Ala Ala Phe Asn Glu Gln
210                 215                 220 acc gac tgg ttg atc aag cac gcc agg ctg gac cgc agc aag ctc acc      720
Thr Asp Trp Leu Ile Lys His Ala Arg Leu Asp Arg Ser Lys Leu Thr
225                 230                 235                 240 ctg cac gcc gcc aac tcg ttc gct acg ctg gaa gtg ccg gaa gcg cgc      768
Leu His Ala Ala Asn Ser Phe Ala Thr Leu Glu Val Pro Glu Ala Arg
                245                 250                 255 ctg gac atg gta cga acg ggt ggc gcg ctg ttc ggc gac acc gtg ccg      816
Leu Asp Met Val Arg Thr Gly Gly Ala Leu Phe Gly Asp Thr Val Pro
            260                 265                 270 gcg cgc acc gag tac aaa cgt gcg atg cag ttc aaa tcg cac gtg gcg      864
Ala Arg Thr Glu Tyr Lys Arg Ala Met Gln Phe Lys Ser His Val Ala
        275                 280                 285 gcg gtg cac agc tat ccg gcc ggc aac acc gtg ggc tat gac cgc acc      912
Ala Val His Ser Tyr Pro Ala Gly Asn Thr Val Gly Tyr Asp Arg Thr
290                 295                 300 ttc acc ctg gcc cgt gat tcg cgg ctg gcc aac att acg gtc ggg tac      960
Phe Thr Leu Ala Arg Asp Ser Arg Leu Ala Asn Ile Thr Val Gly Tyr
305                 310                 315                 320 tcc gat ggc tac cgc cgg gta ttc acc aac aag ggc cat gtg ctg atc     1008
Ser Asp Gly Tyr Arg Arg Val Phe Thr Asn Lys Gly His Val Leu Ile
                325                 330                 335 aac ggc cac cgt gtg ccg gtc gtg ggc aag gtg tcg atg aac acg ctg     1056
Asn Gly His Arg Val Pro Val Val Gly Lys Val Ser Met Asn Thr Leu
            340                 345                 350 atg gtc gat gtc acc gac ttc cct gat gtg aag ggg ggt aac gaa gtg     1104
```

```
                Met Val Asp Val Thr Asp Phe Pro Asp Val Lys Gly Gly Asn Glu Val
                                355                 360                 365 gtg ctg ttc ggc aag cag gcc ggg ggc gaa atc acc cag gcc gag atg        1152
Val Leu Phe Gly Lys Gln Ala Gly Gly Glu Ile Thr Gln Ala Glu Met
    370                 375                 380 gaa gaa atc aac ggc gcg ttg ctc gcc gat ttg tac acc gta tgg ggc        1200
Glu Glu Ile Asn Gly Ala Leu Leu Ala Asp Leu Tyr Thr Val Trp Gly
385                 390                 395                 400 aat tcc aac ccg aag ata ctc gtc gac                                    1227
Asn Ser Asn Pro Lys Ile Leu Val Asp
                405

<210> SEQ ID NO 4
<211> LENGTH: 1227
<212> TYPE: DNA
<213> ORGANISM: Pseudomonas putida IFO12296

<400> SEQUENCE: 4 atg caa ttt agc cgt acc ctc ctg gct gca tcc ctc gct ctg ctg atc        48
Met Gln Phe Ser Arg Thr Leu Leu Ala Ala Ser Leu Ala Leu Leu Ile
1               5                   10                  15 act ggc cag gcc ccg ctg tac gcc gca ccg ccc ctg tcg atg gac aac        96
Thr Gly Gln Ala Pro Leu Tyr Ala Ala Pro Pro Leu Ser Met Asp Asn
            20                  25                  30 ggc acc acc gcc ctg acc gcg cag aac agc aac gcc tgg gtc gaa atc       144
Gly Thr Thr Ala Leu Thr Ala Gln Asn Ser Asn Ala Trp Val Glu Ile
        35                  40                  45 agt gcc ggc gca ctg caa cac aac atc cgt acc ttg cag gcc gag ttg       192
Ser Ala Gly Ala Leu Gln His Asn Ile Arg Thr Leu Gln Ala Glu Leu
    50                  55                  60 ggc ggc aag tcc aag ctg tgc gcc gtg ctc aag gcc gac gcc tat ggc       240
Gly Gly Lys Ser Lys Leu Cys Ala Val Leu Lys Ala Asp Ala Tyr Gly
65                  70                  75                  80 cac ggt atc ggc ctg gtg atg ccg tcg atc atc gcc cag ggc gtg ccc       288
His Gly Ile Gly Leu Val Met Pro Ser Ile Ile Ala Gln Gly Val Pro
                85                  90                  95 tgc gtg gcg gtg gcc agc aac gag gag gca cgc gtg gtc cgc gcc agt       336
Cys Val Ala Val Ala Ser Asn Glu Glu Ala Arg Val Val Arg Ala Ser
            100                 105                 110 ggc ttc acc ggg caa ctg gtg cgg gta cgc ctg gcc agc ctc ggc gaa       384
Gly Phe Thr Gly Gln Leu Val Arg Val Arg Leu Ala Ser Leu Gly Glu
        115                 120                 125 gtg gaa gat gcc ttg cag tac gac atg gaa gag ctg gtt ggc agc gcc       432
Val Glu Asp Ala Leu Gln Tyr Asp Met Glu Glu Leu Val Gly Ser Ala
    130                 135                 140 gag ttc gcc cgc cag ctc gat gcc atc gcc gaa cgc cac ggc aag acc       480
Glu Phe Ala Arg Gln Leu Asp Ala Ile Ala Glu Arg His Gly Lys Thr
145                 150                 155                 160 ctg cgc att cac atg gcg ctc aat tcc agc ggc atg agc cgc aac ggc       528
Leu Arg Ile His Met Ala Leu Asn Ser Ser Gly Met Ser Arg Asn Gly
                165                 170                 175 gtg gaa atg acc acc tgg tcc ggc cgg ggt gaa gcg ctg cag atc act       576
Val Glu Met Thr Thr Trp Ser Gly Arg Gly Glu Ala Leu Gln Ile Thr
            180                 185                 190 gac cag aag cac ctc cag ctg gtc gcg ctg atg act cac ttc gcc gtg       624
Asp Gln Lys His Leu Gln Leu Val Ala Leu Met Thr His Phe Ala Val
        195                 200                 205 gaa gac aag gac gat gtg cgc aaa ggc ctg gca gcg ttc aac gaa cag       672
Glu Asp Lys Asp Asp Val Arg Lys Gly Leu Ala Ala Phe Asn Glu Gln
    210                 215                 220
```

```
acc gac tgg ctg atc aag cac gcg aag ctt gat cgc agc aag ctc acc        720
Thr Asp Trp Leu Ile Lys His Ala Lys Leu Asp Arg Ser Lys Leu Thr
225                 230                 235                 240 ctg cat gcc gcc aac tcc ttc gct acg ctg gaa gtg ccg gaa gcg cac        768
Leu His Ala Ala Asn Ser Phe Ala Thr Leu Glu Val Pro Glu Ala His
            245                 250                 255 ctg gac atg gtg cgt acc ggt ggc gcg ctg ttc ggc gac acc gtg ccg        816
Leu Asp Met Val Arg Thr Gly Gly Ala Leu Phe Gly Asp Thr Val Pro
        260                 265                 270 acg cgc acc gaa tac caa cgt gtc atg cag ttc aag tcg cac gtg gcg        864
Thr Arg Thr Glu Tyr Gln Arg Val Met Gln Phe Lys Ser His Val Ala
    275                 280                 285 gcg gtg cac agc tac ccg gca ggc aac acc gtc ggc tac gac cgc acc        912
Ala Val His Ser Tyr Pro Ala Gly Asn Thr Val Gly Tyr Asp Arg Thr
290                 295                 300 ttc acc ctg gcg cgt gat tcg cgc ctg gcc aac atc acc gtg ggt tac        960
Phe Thr Leu Ala Arg Asp Ser Arg Leu Ala Asn Ile Thr Val Gly Tyr
305                 310                 315                 320 tcc gat ggc tac cgc cgg gtg ttc acc aac aag ggc cat gtg ctg atc       1008
Ser Asp Gly Tyr Arg Arg Val Phe Thr Asn Lys Gly His Val Leu Ile
            325                 330                 335 aac ggc cac cga gtg cca gtg gtg ggc aag gtg tcg atg aac acc ttg       1056
Asn Gly His Arg Val Pro Val Val Gly Lys Val Ser Met Asn Thr Leu
        340                 345                 350 atg gtc gat gtc acc gat ttc ccc gat gtg aag ggg ggc aac gaa gtg       1104
Met Val Asp Val Thr Asp Phe Pro Asp Val Lys Gly Gly Asn Glu Val
    355                 360                 365 gtg ctg ttc ggc aaa cag gcc ggg agg gag atc acc cag gcc gag ata       1152
Val Leu Phe Gly Lys Gln Ala Gly Arg Glu Ile Thr Gln Ala Glu Ile
370                 375                 380 gaa gaa atc aac ggc gcg ctg ctc gcc gac ctc tac acc gta tgg ggc       1200
Glu Glu Ile Asn Gly Ala Leu Leu Ala Asp Leu Tyr Thr Val Trp Gly
385                 390                 395                 400 agt tcc aac ccg aag att ctc gtc gac                                   1227
Ser Ser Asn Pro Lys Ile Leu Val Asp
            405

<210> SEQ ID NO 5
<211> LENGTH: 14
<212> TYPE: PRT
<213> ORGANISM: Pseudomonas putida
<220> FEATURE:
<221> NAME/KEY: unsure
<222> LOCATION: (10)
<223> OTHER INFORMATION: Xaa represents unsure

<400> SEQUENCE: 5

Ala Val Leu Lys Ala Asp Ala Tyr Gly Xaa Gly Ile Gly Leu
1               5                   10

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 6
cccaagctta tgcccttcg ccgtaccctt c                                       31

<210> SEQ ID NO 7
<211> LENGTH: 31
```

```
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 7
cgcggatcct cagtcgacga gtatcttcgg g                               31

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 8
gtaaaaagag aaatcaccat gcaatttagc cgtacc                          36

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 9
cgcggatcct cagtcgacga gaatcttcgg g                               31
```